United States Patent
Wagner et al.

(10) Patent No.: US 10,856,860 B2
(45) Date of Patent: Dec. 8, 2020

(54) TROCAR SLEEVE, TROCAR SYSTEM AND METHOD OF MANUFACTURING A TROCAR SLEEVE

(71) Applicant: Karl Storz GmbH & Co. KG, Tuttlingen (DE)

(72) Inventors: Sebastian Wagner, Bretten (DE); Michael Sauer, Tuttlingen (DE); Alexander Fuchs, Steisslingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 366 days.

(21) Appl. No.: 15/416,257

(22) Filed: Jan. 26, 2017

(65) Prior Publication Data
US 2017/0209134 A1 Jul. 27, 2017

(30) Foreign Application Priority Data
Jan. 27, 2016 (DE) .......... 10 2016 101 462

(51) Int. Cl.
*A61B 17/02* (2006.01)
*A61B 17/34* (2006.01)
*A61B 17/00* (2006.01)

(52) U.S. Cl.
CPC .......... *A61B 17/0218* (2013.01); *A61B 17/34* (2013.01); *A61B 17/3462* (2013.01);
(Continued)

(58) Field of Classification Search
CPC .............. A61B 17/0218; A61B 17/34; A61B 17/3415; A61B 17/3462; A61B 17/3468;
(Continued)

(56) References Cited

U.S. PATENT DOCUMENTS 4,716,901 A * 1/1988 Jackson ............. A61B 17/3439
128/200.26
5,258,003 A * 11/1993 Ciaglia ............. A61B 17/3401
604/164.11
(Continued)

FOREIGN PATENT DOCUMENTS

DE 2218901 A1 10/1973
DE 4312147 A1 10/1993
(Continued)

OTHER PUBLICATIONS

European Search Report Application No. 17153122.1 dated Jun. 27, 2017; Completed Date: Jul. 6, 2017 7 Pages.
(Continued)

*Primary Examiner* — Jocelin C Tanner
(74) *Attorney, Agent, or Firm* — Whitmyer IP Group LLC

(57) ABSTRACT

A trocar sleeve comprises a flexible hollow shaft comprising a distal end and a proximal end, and a handling head that is formed at the proximal end of the hollow shaft. The trocar sleeve is manufactured from an elastomer material. The hollow shaft comprises an inner contour that is adapted to an outer contour of a trocar mandrel in such a way that the trocar sleeve and the trocar mandrel are arranged to be coupled to one another while generating a defined preload to stabilize the trocar sleeve. A trocar system comprises a trocar sleeve and a trocar mandrel that is arranged to be inserted in the trocar sleeve, while generating a defined preloading in the trocar sleeve. A method of manufacturing a trocar sleeve involves integrally forming a hollow shaft and a handling head in a common mold by molding.

18 Claims, 8 Drawing Sheets

(52) U.S. Cl.
CPC ...... *A61B 17/3468* (2013.01); *A61B 17/3415* (2013.01); *A61B 2017/00526* (2013.01); *A61B 2017/0225* (2013.01); *A61B 2017/3419* (2013.01); *A61B 2017/3433* (2013.01)

(58) Field of Classification Search
CPC ............ A61B 17/3401; A61B 17/3421; A61B 2017/00526; A61B 2017/0225; A61B 2017/3419; A61B 2017/3433; A61B 2017/3435
See application file for complete search history.

(56) References Cited

U.S. PATENT DOCUMENTS

| | | | | |
|---|---|---|---|---|
| 5,380,288 | A | * | 1/1995 | Hart ................... A61B 17/3462 277/503 |
| 5,391,156 | A | * | 2/1995 | Hildwein ............... A61B 17/29 604/174 |
| 5,423,848 | A | | 6/1995 | Washizuka et al. |
| 5,749,892 | A | * | 5/1998 | Vierra ................ A61B 17/0469 600/201 |
| 5,817,062 | A | * | 10/1998 | Flom .................. A61B 17/3417 604/174 |
| 5,843,039 | A | * | 12/1998 | Klemm ............... A61B 17/3417 604/164.01 |
| 6,162,236 | A | * | 12/2000 | Osada ................ A61B 17/3439 604/264 |
| 2003/0093104 | A1 | | 5/2003 | Bonner et al. |
| 2006/0074374 | A1 | * | 4/2006 | Gresham ............ A61B 17/3474 604/26 |
| 2009/0043328 | A1 | * | 2/2009 | Delsman ............ A61B 17/3415 606/185 |
| 2010/0100045 | A1 | * | 4/2010 | Pravongviengkham ..................... A61B 17/3421 604/164.09 |
| 2010/0318033 | A1 | * | 12/2010 | Lam ................... A61B 17/3421 604/164.11 |
| 2015/0164547 | A1 | * | 6/2015 | Sauter ................ A61B 17/3421 600/204 |

FOREIGN PATENT DOCUMENTS

| | | |
|---|---|---|
| DE | 4234990 A1 | 4/1994 |
| DE | 10156312 A1 | 6/2003 |
| DE | 102011107615 A1 | 1/2013 |
| DE | 102014114890 A1 | 4/2016 |
| EP | 0535974 A1 | 4/1993 |
| EP | 2090258 A1 | 8/2009 |
| EP | 3009088 A1 | 4/2016 |
| WO | 2007057127 A1 | 5/2007 |
| WO | 2013135354 A2 | 9/2013 |

OTHER PUBLICATIONS

German Examination Report Application No. 10 2016 101 462.1 Completed: Sep. 9, 2016 7 Pages.

* cited by examiner

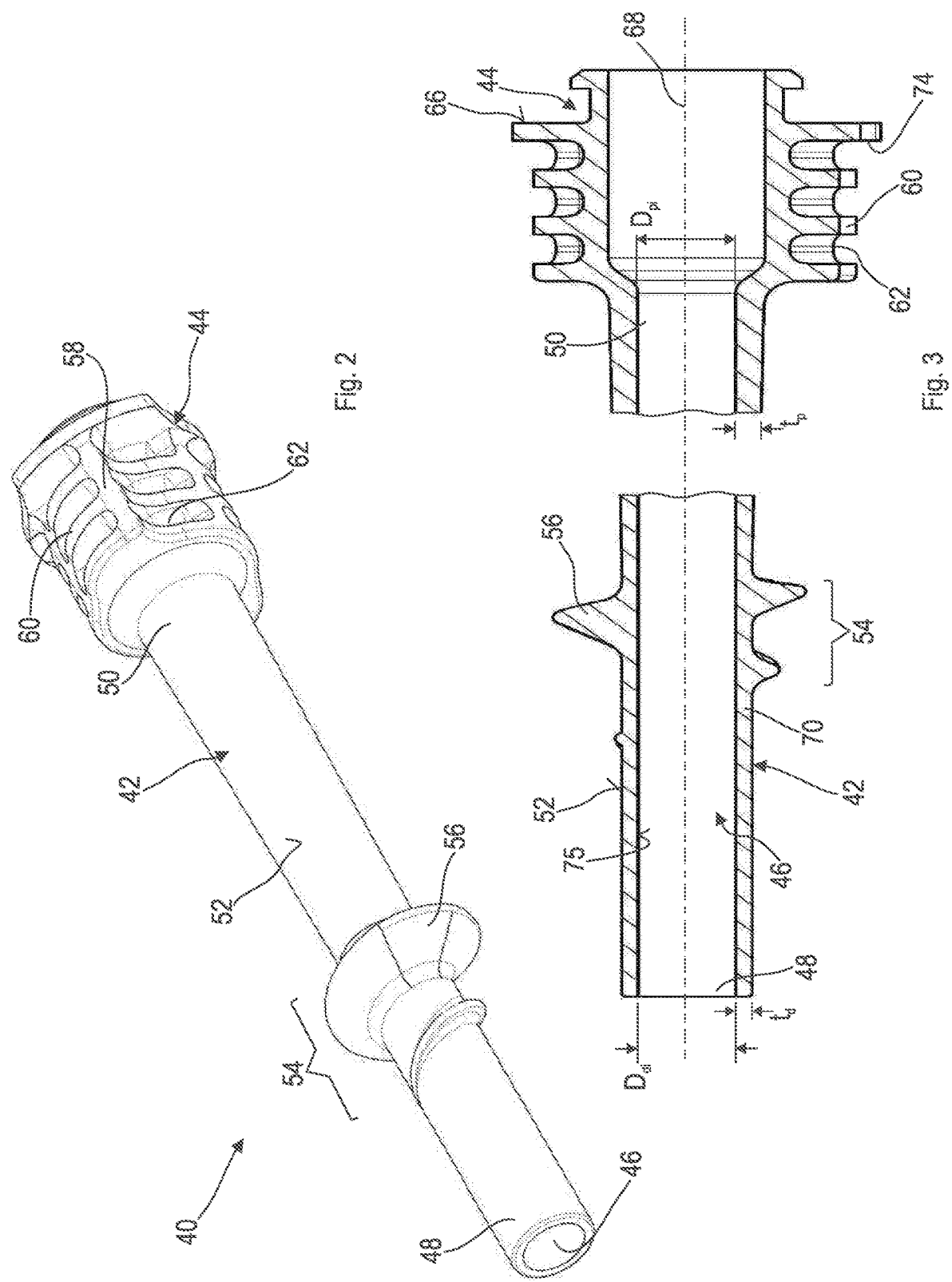

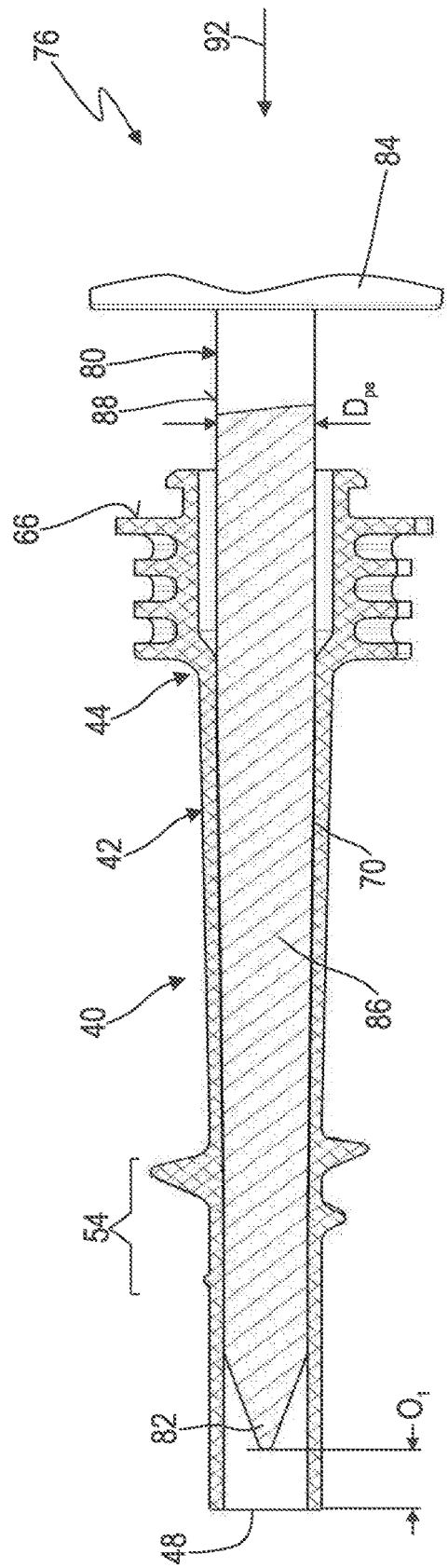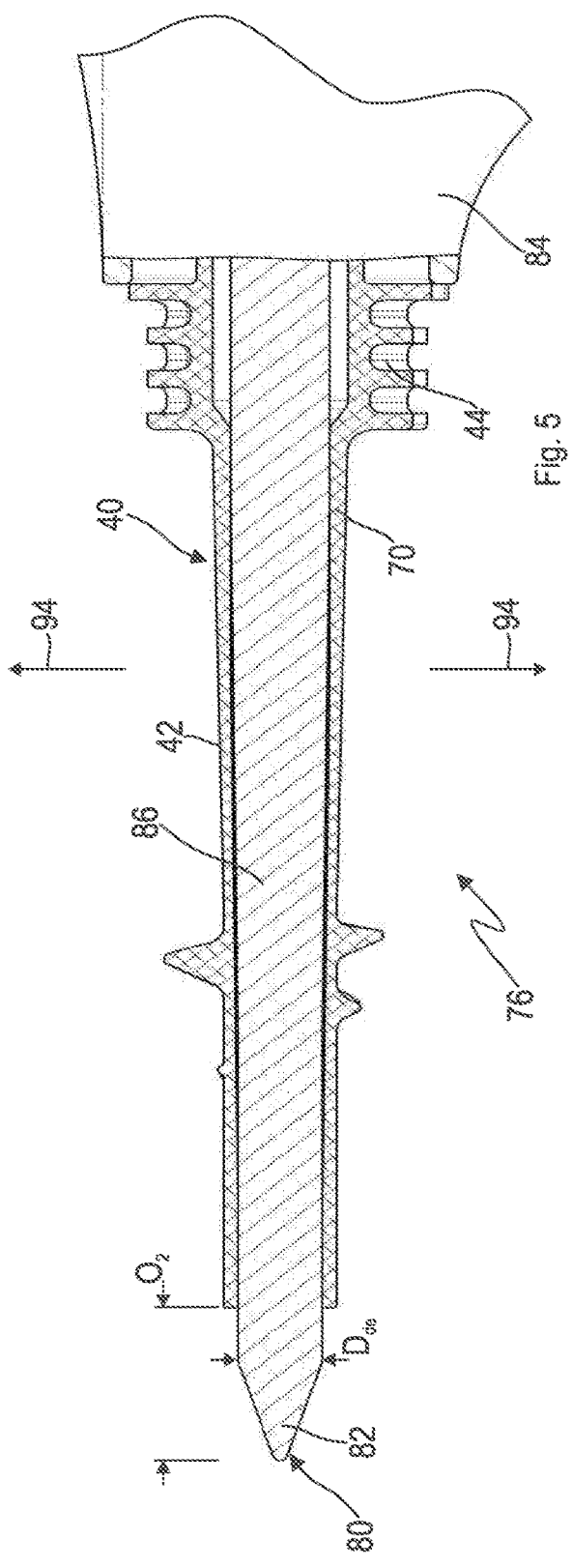

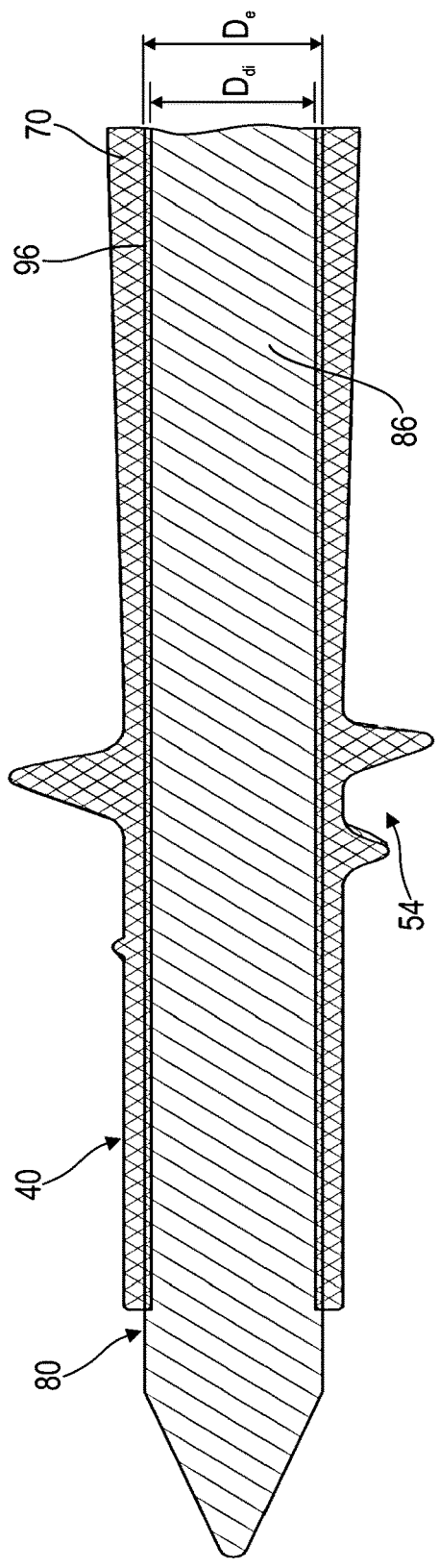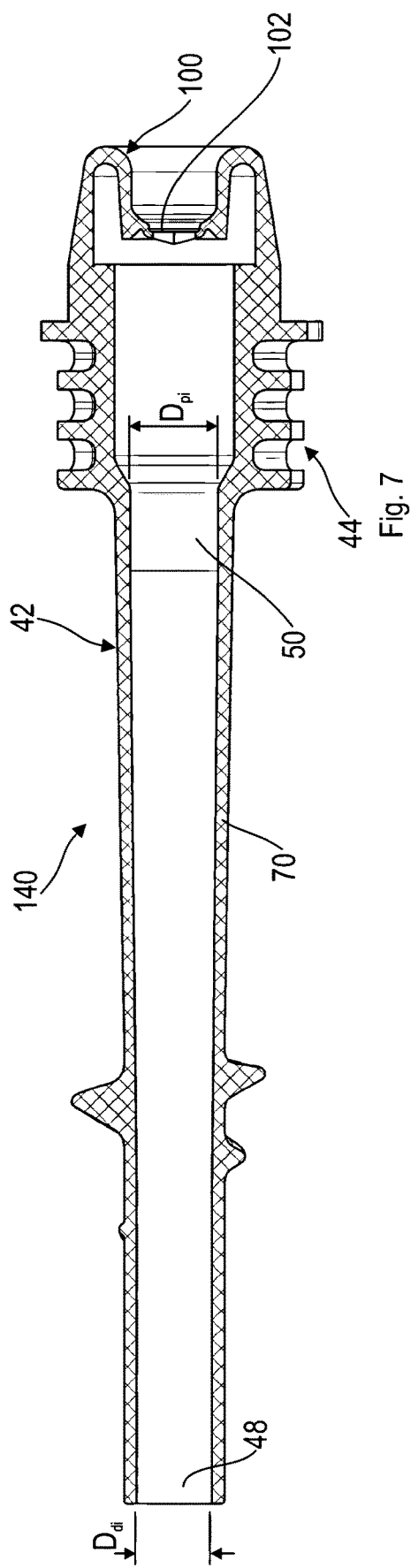

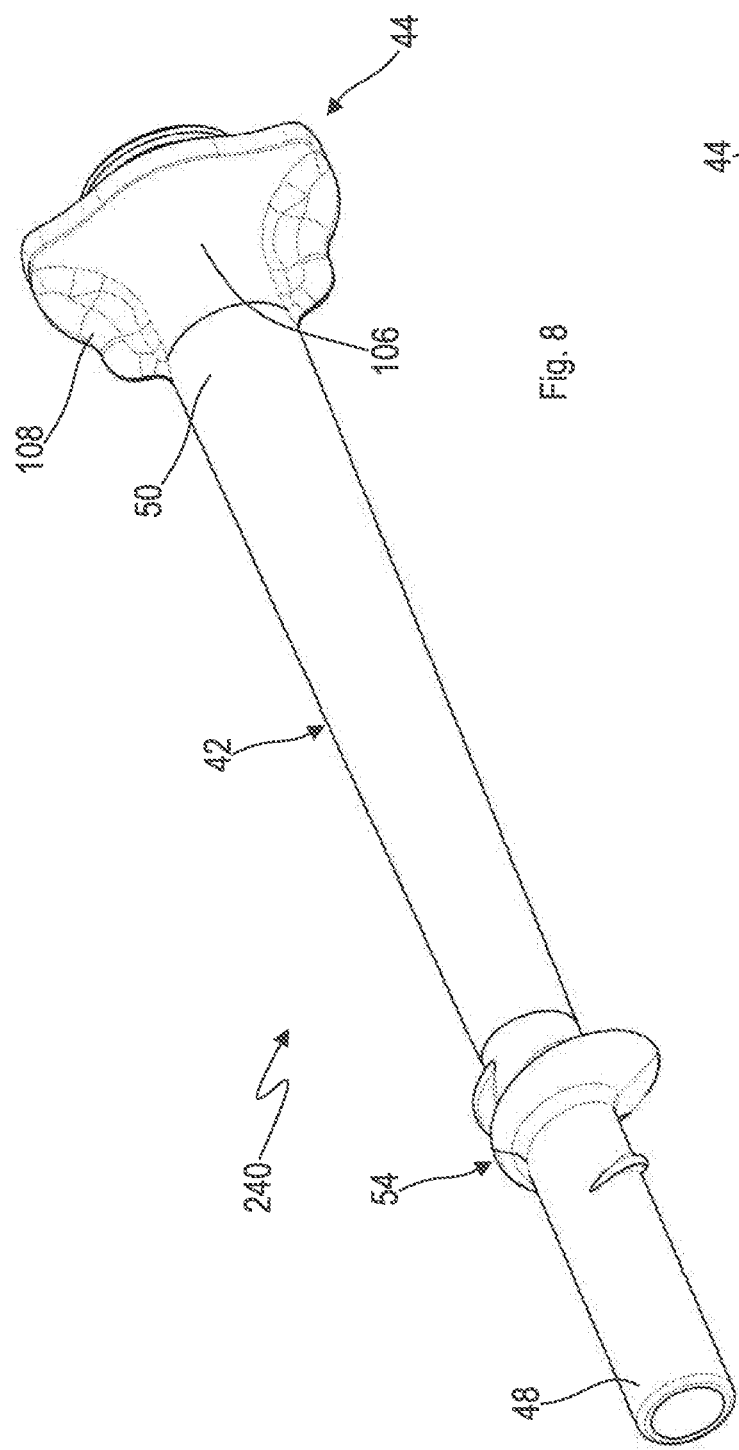
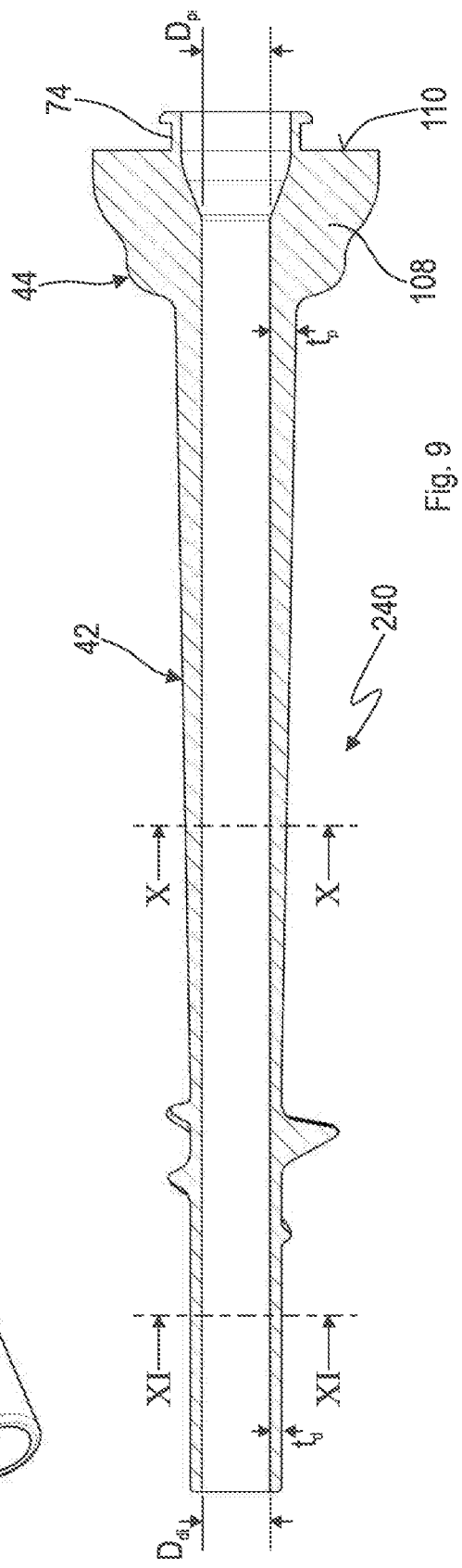

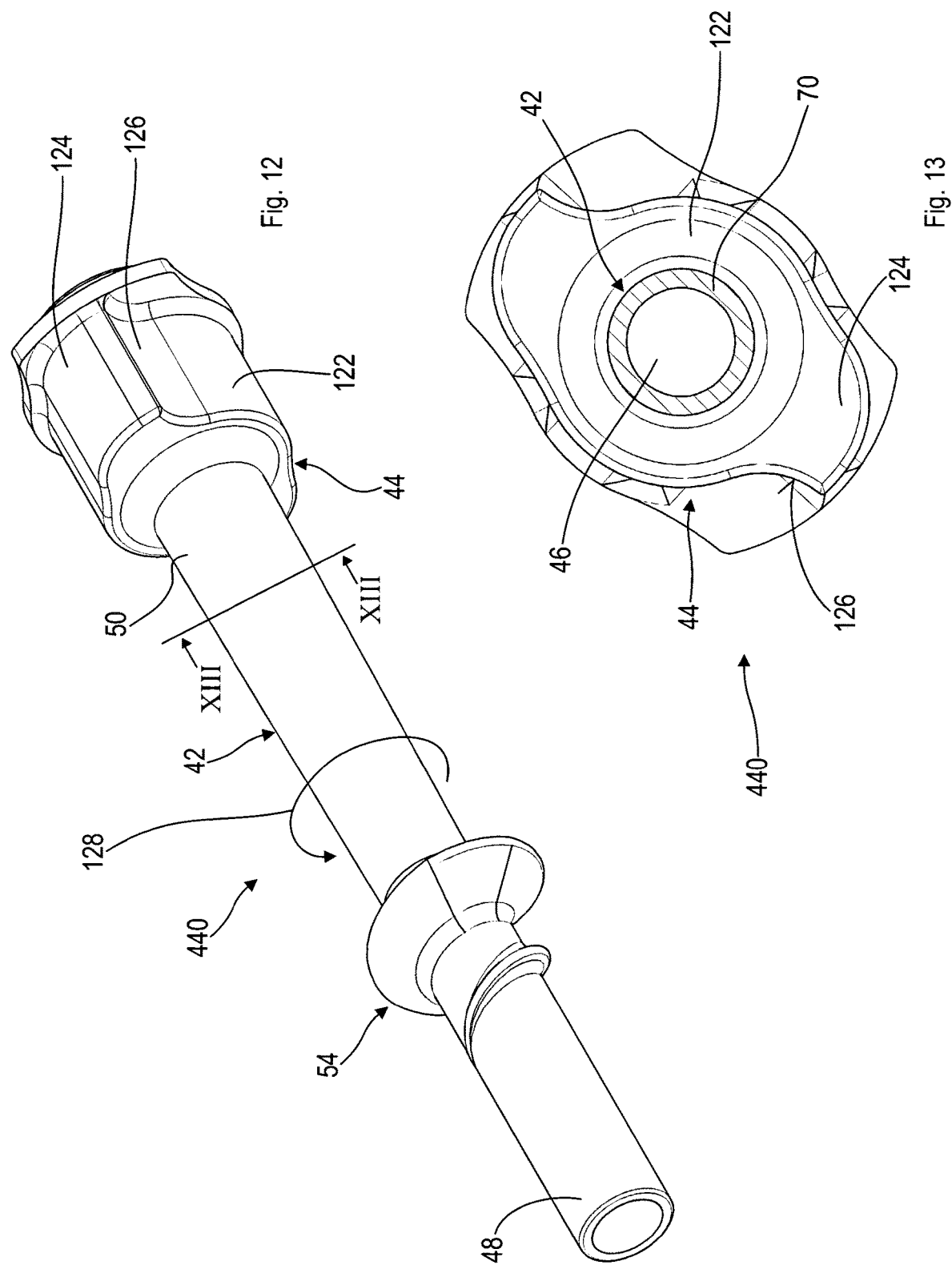

TROCAR SLEEVE, TROCAR SYSTEM AND METHOD OF MANUFACTURING A TROCAR SLEEVE

CROSS-REFERENCES TO RELATED APPLICATIONS

This application claims priority from German patent application 10 2016 101 462.1, filed on Jan. 27, 2016. The entire content of that priority application is fully incorporated by reference herewith.

BACKGROUND

The present disclosure relates to a trocar sleeve having a flexible hollow shaft comprising a distal end and a proximal end, and a handling head that is formed at the proximal end of the hollow shaft. The present disclosure further relates to a trocar system that is provided with a trocar sleeve that is configured to be coupled with a trocar mandrel that is arranged to be inserted in the trocar sleeve. In exemplary embodiments, the disclosure further relates to a method of manufacturing a trocar sleeve and to a method of providing a trocar system.

U.S. Pat. No. 5,383,861 A discloses a flexible trocar sleeve comprising a tube and an attachment part, wherein a distal region of the tube is arranged to be inserted through a trocar puncture site into the interior of the body, wherein the attachment part is mounted to a proximal end of the tube, wherein the attachment part comprises an opening at its proximal front face to which a seal is associated, and wherein the tube is composed of a flexible material. For coupling the tube and the attachment part, an intermediate tube is provided.

Generally, trocar sleeves are used to provide an access to a body cavity in a minimally-invasive procedure. Trocar systems comprising trocar sleeves and trocar mandrels are used, for instance, in the field of laparoscopy to provide an access to the abdominal cavity. To this end, the trocar sleeve comprises a hollow shaft. When placing the trocar sleeve, the trocar system is placed via an incision in the abdominal wall or generally in a tissue and pushed therethrough. Thereafter, the distal end of the shaft extends into the abdominal cavity, and the proximal end protrudes from an upper side of the abdominal wall or the tissue. From the point of view of a user or operating surgeon, the distal end of a distal end is the end facing away from the operating surgeon. The proximal end is the end that is facing the operating surgeon.

The combination of trocar sleeve and trocar mandrel is generally referred to as trocar and/or trocar system. Embodiments of trocar systems comprise a trocar sleeve and a trocar mandrel that is arranged to be pushed into the hollow shaft of the trocar sleeve. Generally, the trocar mandrel comprises at its distal end a tip. The tip extends beyond the distal end of the trocar sleeve when the trocar mandrel is completely pushed therein. The trocar sleeve and the trocar mandrel may be pushed together through the abdominal wall or another tissue to perform an access opening. Having placed the trocar sleeve, the trocar mandrel is pushed away and/or extracted. Hence, through the remaining cavity in the hollow shaft, instruments may be inserted in the body cavity or body opening.

Trocar sleeves may further comprise a proximal head part which also in the mounted state of the trocar sleeve generally does not penetrate into the interior of the body. The head part may also be referred to as handling head. By way of example, the head part comprises ports to lead an insufflation gas, irrigation fluids or such like through the trocar sleeve. Furthermore, at the head part itself or at least adjacent to the head part a sealing arrangement may be provided at the trocar sleeve to enable a closing off and/or a sealing of the trocar system.

Conventional trocar sleeves, particularly the hollow shafts thereof, may be basically formed from a sufficiently stiff and rigid material, particularly from metal material. However, so-called flexible trocar sleeves and/or trocar sleeves having flexible hollow shafts are known that are deformable and/or bendable. This is useful when guiding bent instruments and/or deflectable instrument shafts therefore, for instance.

Flexible hollow shafts of that kind may be manufactured from thermoplastic or thermosetting materials, for instance. Generally, a trocar sleeve of that kind is arranged as an assembled, multi-part trocar sleeve, wherein at least the head part and the hollow shaft are separate components that are mounted to one another.

Further exemplary embodiments of trocar sleeves comprising a thread section that is displaced from the proximal end of the trocar sleeve towards the distal end. In other words, a thread section of that kind, which is for instance helically shaped, may be provided along the longitudinal extension of the hollow shaft and may, departing from the hollow shaft, outwardly protrude in a helical fashion. A trocar sleeve having such an arrangement is described in U.S. patent application Ser. No. 14/881,931, Publication No. US 2016/0100856 A1, the entire content of which is fully incorporated by reference herewith.

By way of example, the helix is formed at a longitudinal section of the hollow shaft that is displaced from the head part in such a way that the inserted trocar sleeve is supported outside the body by the head part and inside the body by the helix, wherein in the mounted state a tissue layer (for instance the abdominal wall) is placed between the helix and the head part. Hence, the helix may provide an inner support surface. The head part may provide an outer support surface. Further embodiments may be envisaged therein between the helix and the head part a further thread section (or, overall, a continuous thread) is formed which receives a kind of lock nut for fixing the trocar sleeve between the helix and the lock nut.

In this connection, exemplary reference is made to German Patent Application, Publication Number DE 101 56 312 A1, disclosing a shaft for a surgically formed access, wherein the shaft comprises, at the distal end thereof, at its outer surface a thread coil.

Conventional trocar sleeves having a hollow shaft that are at least sufficiently flexible generally comprise a multi-piece structure, particularly concerning the connection between the hollow shaft and the head part. There is often a discrepancy between the desired huge flexibility and the stability of the hollow shaft that is necessary at the same time.

Further, trocar sleeves are known having hollow shafts shaped as corrugated tubes. This arrangement (corrugated tubes) increases the flexibility of the hollow shaft. A helical spiral profile having an elevation at the outer side of the hollow shaft and a corresponding depression at the inner side of the hollow shaft may have the same result, wherein the wall thickness of the hollow shaft may be retained basically constant. In other words, the outer wall of the hollow shaft extends in a meandering pattern. Both measures have the drawback that a relative movement between the instrument and the hollow shaft is complicated as the inner contour of the hollow shaft is not smooth. Further, hollow shafts shaped in this way are prone to kinking and/or the formation of wrinkles.

In view of this, it is an object of the present disclosure to present a trocar sleeve that is considerably flexible and suitable for bent or curved instruments.

It is a further object of the present disclosure to present a trocar sleeve that is sufficiently rigid and stiff to simplify a defined placement of the trocar and the insertion of the trocar sleeve, respectively.

It is a further object of the present disclosure to present a trocar sleeve that is easy to manufacture and, at least in some embodiments, suitable for large scale production.

It is a further object of the present disclosure to present a trocar sleeve that can be manufactured while avoiding or, at least, reducing additional assembly steps and manufacturing steps, respectively.

It is a further object of the present disclosure to present a trocar sleeve that is configured to provide additional functions.

It is a further object of the present disclosure to present a trocar sleeve that exhibits a considerable biological compatibility. It is desirous, in exemplary embodiments, to provide an arrangement wherein structural interfaces between involved components can be largely avoided.

It is a further object of the present disclosure to present a trocar system comprising a trocar sleeve and a trocar mandrel that are adapted to one another to stabilize the trocar sleeve.

It is a further object of the present disclosure to present a corresponding method of manufacturing a trocar sleeve.

It is a further object of the present disclosure to present a method of providing a trocar system comprising a flexible trocar sleeve and a trocar mandrel that are adapted to one another and arranged to be coupled to stabilize the trocar sleeve.

SUMMARY

In regard of the trocar sleeve, these and other objects are achieved in that the trocar sleeve is manufactured from an elastomer material, wherein the hollow shaft comprises an inner contour that is adapted to an outer contour of a trocar mandrel in such a way that the trocar sleeve and the trocar mandrel are arranged to be coupled to one manufacturing while generating a defined preload to stabilize the trocar sleeve.

In accordance with the above aspect, the trocar sleeve is namely arranged such that due to the interaction with the trocar mandrel, a defined, at least partial widening (outwardly directed radial expansion) is formed that induces a preloading. The preloading stiffens the trocar sleeve and/or increases the strength the trocar sleeve, for instance at the hollow shaft. In this way, the trocar sleeve may be subject to compression loads, pull loads and/or torsional loads with respect to its longitudinal axis, without generating excessive deformations, buckling, and such like. Having placed the trocar sleeve, the trocar mandrel may be removed. In this way, the widening is reverted and the preloading is relieved. Hence, in certain embodiments, a great flexibility/deformability of the hollow shaft may be provided. The preloading may be regarded as a mechanical preloading and, hence, as a prestress in the hollow shaft of the trocar sleeve.

In this way, the trocar sleeve on the one hand may be extremely flexible. On the other hand, a significantly increased stiffness is provided when the trocar mandrel is inserted in the hollow shaft in a defined manner. The trocar sleeve may be guided in a defined manner.

In other words, the inner contour of the hollow shaft is deliberately formed to be slightly too small for a present outer contour of the trocar mandrel. In this way, the inner contour and hence the complete hollow shaft may be widened to a nominal dimension that is predetermined by the outer contour of the trocar mandrel. In other words, the inner contour has, in the unloaded state, a defined interference with respect to the outer contour of the trocar mandrel.

In accordance with the above aspect, the trocar sleeve may be formed without separate support elements and may comprise a huge stability only through the insertion of the trocar mandrel. This is useful for the envisaged integral arrangement of the trocar sleeve. The trocar sleeve comprises a huge inherent stability when the flexible hollow shaft is at least sectionally widened by the trocar mandrel.

The inner contour of the hollow shaft may be arranged as a through hole or a through channel, for instance. The inner contour may basically comprise a round cross-section. Other cross-sectional shapes may be envisaged. The trocar mandrel generally comprises an outer contour that is adapted to the inner contour of the hollow shaft. Accordingly, also the trocar mandrel may comprise an outer contour having round or circular cross-sections. However, it may be also envisaged to arrange the hollow shaft and the trocar mandrel in such a way that at the inner contour and the outer contour non-corresponding and/or non-congruent cross-sections are present. By way of example, the trocar mandrel may comprise an oval cross-section, at least sectionally, whereas the inner contour of the hollow shaft comprises a circular cross-section or at least an oval cross-section having a side ratio that differs from the side ratio of the cross-section of the outer contour.

It goes without saying that the hollow shaft does not have to be widened entirely along its longitudinal extension by the trocar mandrel. Rather, it may be envisaged that the hollow shaft is sectionally widened along its longitudinal extension and/or sectionally along its circumferential extension by the trocar mandrel.

The flexible hollow shaft is configured for receiving a trocar mandrel and for guiding instruments therethrough. The interference and/or widening may be influenced by inserting the trocar mandrel in the hollow shaft in a defined manner. By way of example, the widening of the inner contour of the hollow shaft may be dependent on an axial relative position between the trocar mandrel and the hollow shaft. In an exemplary embodiment, this applies when at least the inner contour or the outer contour is at least sectionally conically or spherically shaped.

In an exemplary embodiment of the trocar sleeve, the hollow shaft is at least sectionally widened in a defined axial relative position between the trocar sleeve and the trocar mandrel. This applies to a state in which the trocar mandrel is inserted in the trocar sleeve, for instance. In this way, a combination may be formed to insert the trocar sleeve at least partially in the interior of the body through the abdominal wall or the tissue.

In an exemplary embodiment, the elastomer material involves a material having a Shore hardness of no more than 90 Shore A. Elastomer materials generally involve materials that are sufficiently form stable but nevertheless elastically deformable. Generally, elastomers are used in a temperature range that is higher than the glass transition temperature and/or the glass transition point. Elastomer materials generally exhibit rubber-elastic properties.

By way of example, at least the hollow shaft, for instance the inner contour thereof, or the trocar mandrel, for instance the outer contour thereof, may be at least sectionally tapered. In other words, at least the cross-section of the inner contour or the cross-section of the outer contour may be tapered from the proximal end towards the distal end. Accordingly, based on a selected axial offset between the trocar mandrel and the trocar sleeve, the level of the interference and/or the widening may be determined. Hence, also the level of the preloading in the hollow shaft of the trocar sleeve may be influenced. The greater the preloading of the hollow shaft, the greater is the inherent stability during insertion in the interior of the body.

It is conceivable to provide a single defined axial relative position which basically results in just one defined interference and hence a defined preloading. This may be for instance achieved by appropriate limit stops to delimit the axial insertion and/or penetration of the trocar mandrel in relation to the trocar sleeve. Conversely, it is conceivable to deliberately provide no limit stop to enable a variation of the axial relative position (of the axial offset) and hence of the preloading.

According to a further exemplary embodiment, the Shore hardness of the elastomer material, determined in accordance with International Standard ISO 7619-1 (ISO 7619-1:2010), is no more than 90 Shore A. In an exemplary embodiment, the hardness is no more than 70 Shore A. A minimum value for the hardness may be for instance about 50 Shore A. Ranges for the Shore hardness of the elastomer material that are conceivable may be, at least in accordance with some exemplary embodiments, between 50 and 90 Shore A. In an exemplary embodiment, the hardness is between 50 and 70 Shore A. The lower the value of the Shore hardness is, the weaker are the cross-links of the materials, and the softer is the material.

In an exemplary embodiment, the hardness of the elastomer material is approximately 70 Shore A or, more specifically, is 70 Shore A. It is to be noted that these indications generally involve standard tolerances that are present when processing and forming parts from elastomer material. In an exemplary embodiment, the hardness of the elastomer material is between 65 and 75 Shore A.

According to a further exemplary embodiment of the trocar sleeve, at least the hollow shaft and the handling head are formed in one piece. In an exemplary embodiment, the trocar sleeve is integrally shaped and manufactured by casting or molding. In this way, the manufacturing effort and, in some embodiments, the assembly effort may be considerably reduced. In an exemplary embodiment, the trocar sleeve is entirely or nearly entirely integrally manufactured. In an exemplary embodiment, the hollow shaft and the handling head are integrally shaped and jointly manufactured. In an exemplary embodiment, the handling head may be equipped with further elements, for instance with sealing arrangements, ports, valves and such like.

Nevertheless, the common, integral arrangement of the hollow shaft and the handling head from the elastomer material results in a manufacturing optimization. There is no structural interface between the hollow shaft and no interface between different materials at the transition between the hollow shaft and the handling head. This is useful from a hygienic point of view.

According to a further exemplary embodiment of the trocar sleeve, the elastomer material is selected from the group consisting of the following: silicone, silicone rubber, thermoplastic elastomers (TPE), rubber, and compounds containing the same. Rubber involves synthetic rubber and natural rubber. The elastomer may for instance involve ethylene propylene diene monomer rubber (EPDM).

According to a further exemplary embodiment of the trocar sleeve, the hollow shaft is at least sectionally tubular or cylindrically shaped and comprises, at least sectionally, a smooth elevation-free outer surface. In an exemplary embodiment, the inner contour is at least sectionally provided with a friction-reducing coating. The friction-reducing coating may for instance consist of polytetrafluoroethylene (PTFE), or containing the same. Other substances for friction minimization and/or friction optimization are conceivable.

Further, in exemplary embodiments, at least a contact area of the inner contour of the hollow shaft may be fluoridated to minimize any friction between the hollow shaft and the instruments or/or trocar mandrel to be inserted.

The inner contour of the hollow shaft is, in some exemplary embodiments, at least in the region in which the hollow shaft is contacted by the trocar mandrel, smoothly shaped. In other words, there is no axially extending corrugated profile having circumferential sections and/or no helical grooves provided at the inner contour. This simplifies the handling and feeding-through of instruments through the hollow shaft. In an exemplary embodiment, sticking and/or clamping of instruments are significantly avoided in this way.

In some exemplary embodiments, also the outer contour or outer surface of the hollow shaft is at least sectionally smooth and shaped without elevations. Nevertheless, it goes without saying that at least a thread section at the outer contour of the hollow shaft may be formed. However, the hollow shaft of the trocar sleeve is not provided with a corrugated tube structure, to increase the deformability and/or flexibility. In other words, in an exemplary embodiment, the hollow shaft is shaped in a non-corrugated manner.

According to an exemplary embodiment of the trocar sleeve, the hollow shaft comprises at least sectionally a wall thickness that is increasing from a distal end towards a proximal end. In an exemplary embodiment, a continuous or quasi-continuous increase of the wall thickness may be present. This measure may have the effect that the hollow shaft itself is shaped sufficiently rigid in a transition region with the handling head. The distal end of the hollow shaft which only has a relatively small wall thickness, by contrast, may be simply widened by the trocar mandrel to be inserted, wherein a preloading is generated which increases the strength of the trocar sleeve.

According to a further exemplary embodiment of the trocar sleeve, the inner contour of the hollow shaft is at least sectionally conically or spherically shaped, having an inner diameter that is increasing from a distal end towards a proximal end. In accordance with this embodiment, the distal end of the hollow shaft may be simply widened, whereby the stability of the hollow shaft, in combination with the trocar mandrel, is increased. Further, the hollow shaft may overall be tapered towards the distal end which further simplifies the insertion of the trocar system. According to a refinement of the above embodiment, the inner contour of the hollow shaft is adapted to an at least sectionally conical or spherical arrangement of the outer contour of the trocar mandrel to preload the trocar sleeve in a defined manner when inserting the trocar mandrel. This may also contribute to the desired strength enhancement and/or for increasing the stability of the trocar sleeve.

According to a further exemplary embodiment of the trocar sleeve, a thread section is formed at the hollow shaft, wherein the hollow shaft, the thread section and the handling head are formed in one piece. In an exemplary embodiment, the thread section is formed as an elevation at an outer perimeter of the hollow shaft. The hollow shaft, the thread section and the handling head may be jointly formed from one the same elastomer material.

Further, exemplary embodiments are conceivable, wherein a first and a second thread section are formed at the hollow shaft which are axially displaced from one another. The second thread section may be used to support a lock nut that is receivable between the handling head and the first thread section at the hollow shaft. In this connection, reference is made again to U.S. patent application Ser. No. 14/881,931.

In some exemplary embodiments, a manufacturing method may be selected which also enables the de-molding of shapes that are at least partially provided with undercuts. Insofar, a great freedom of design is possible.

In a further exemplary embodiment, the thread section may comprise at least one turn of the thread the height and pitch is variable. Further, for instance the inclination of flanks of the turn of the thread may be adapted to selected operating conditions. Overall, a thread may be generated that is basically freely definable that, on the one hand, enables a simple insertion, for instance due to a huge pitch and a small height at distal run-out of the thread. Further, the thread may comprise, at its proximal run-out a significantly reduced pitch and a greater height, compared to the distal run-out. This increases the retaining effect, particularly against accidental pulling out or wrapping out of the hollow shaft from the tissue.

According to a further exemplary embodiment of the trocar sleeve, the inner contour of the hollow shaft is at least sectionally shaped non-rotationally symmetric. In an exemplary embodiment, the inner contour comprises a non-circular cross-section perpendicular to the longitudinal direction and/or a longitudinal axis of the hollow shaft corresponding thereto.

In this way, a positive fit secured rotation entrainment may be effected between the hollow shaft of the trocar sleeve and the trocar mandrel. Accordingly, in some embodiments, also the trocar mandrel comprises a corresponding shape that is not rotationally symmetric.

By way of example, the trocar mandrel comprises at least sectionally along its longitudinal extension a ridge-like elevation that is adapted to a ridge-like depression of the hollow shaft and that also extends in the longitudinal direction. Accordingly, a relative rotation between the hollow shaft and the trocar mandrel may be stopped and/or at least reduced.

It is to be noted in this connection that in accordance with at least some exemplary embodiments, it is not necessarily about completely stopping the relative rotation between the trocar mandrel and the hollow shaft. For instance, it is conceivable that the hollow shaft is at least sectionally twisted when the trocar mandrel is rotated about its longitudinal axis. This may be for instance the case when at least sectionally a rotation entrainment of the hollow shaft by the trocar mandrel is present, for instance due to friction between the inner contour and the outer contour. Also the torsion or twisting of the hollow shaft may appropriately cause a preloading at the hollow shaft which results in an increased stability.

For instance, it is conceivable to provide the inner contour of the hollow shaft and the outer contour of the trocar mandrel with an oval cross-section or a similar non-cylindrical cross-section. In this way, on the one hand, an excessive relative rotation between the trocar mandrel and the hollow shaft may be avoided. However, at least within limits, a relative movement involving a partial twisting of the hollow shaft may be effected to increase the rigidity of the hollow shaft.

According to a further exemplary embodiment of the trocar sleeve, a sealing contour or a sealing receiving contour is formed at the proximal end of the hollow shaft, for instance at the handling head. In other words, embodiments may be envisaged, wherein also an elastomer seal may be provided at an integral component of the trocar sleeve. In an exemplary embodiment, the sealing contour is mounted to the handling head. In an alternative embodiment, at least one sealing receiving contour is provided at the handling head, for instance arranged as a circumferential groove for receiving a separate seal.

In regard of the trocar system, the above and other objects of the present disclosure are achieved by a trocar system comprising a trocar sleeve in accordance with the exemplary embodiments described herein, and a trocar mandrel, wherein the trocar mandrel is arranged to be inserted in the trocar sleeve while generating a defined preloading. The trocar mandrel is inserted in the hollow shaft of the trocar sleeve and may at least sectionally widen the same. In this way, the hollow shaft and, hence, the trocar sleeve is stabilized. In an exemplary embodiment, the achievable preloading is dependent on an axial relative position between the trocar mandrel and the hollow shaft.

Generally, the trocar mandrel comprises at its distal end a tip. A shaft adjoins the tip. In an exemplary embodiment, the shaft of the trocar mandrel is at least sectionally conically or spherically shaped. In certain embodiments, a cone-like contour may be present. In this way, the more the trocar mandrel is inserted in the hollow shaft, the more the hollow shaft may be widened.

In regard of the manufacturing method, the above and other objects of the present disclosure are achieved by a method of manufacturing a trocar sleeve, for instance a trocar sleeve in accordance with at least one of the aforementioned embodiments, wherein the method comprises the following steps:

providing a mold that is configured for forming a trocar sleeve having a flexible hollow shaft and a handling head, providing an elastomer material, for instance a material having, in the processed state, a Shore hardness, determined in accordance with ISO 7619-1, of no more than 90 Shore A, preferably no more than 70 Shore A, further preferably no more than 50 Shore A, and molding the trocar sleeve, involving filling the mold, including integrally forming the hollow shaft and the handling head, wherein at the hollow shaft an inner contour is formed that is adapted to an outer contour of a trocar mandrel in such a way that the trocar sleeve and the trocar mandrel are arranged to be coupled to one another while generating a defined preloading to stabilize the trocar sleeve.

In regard of the provision of the trocar system, the above and other objects of the present disclosure are achieved by a method for providing a trocar system is provided, the method comprising the following steps:

manufacturing a trocar sleeve in accordance with the afore-described manufacturing method, providing of a trocar mandrel that is adapted to the trocar sleeve, and inserting the trocar mandrel in the trocar sleeve, involving at least sectionally widening the trocar sleeve, involving generating a preloading, for instance in the hollow shaft the trocar sleeve, for mechanically stabilizing the trocar sleeve.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein:

FIG. 2 is a perspective view of a trocar sleeve, seen from the distal end;

FIG. 3 is a broken longitudinal cross-section through the trocar sleeve according to FIG. 2;

FIG. 4 is a longitudinal cross-section through a trocar system, comprising a trocar sleeve according to FIGS. 2 and 3, and a trocar mandrel, in a first axial relative position;

FIG. 5 shows the trocar system according to FIG. 4 in a second axial relative position;

FIG. 6 is an enlarged partial view of a distal end of a trocar system;

FIG. 7 is a longitudinal cross-section through a further embodiment of a trocar sleeve;

FIG. 8 is a perspective view of a further trocar sleeve, seen from the distal end;

FIG. 9 is a longitudinal cross-section through the trocar sleeve according to FIG. 8;

FIG. 12 is a perspective view of a further embodiment of a trocar sleeve, seen from the distal end;

FIG. 13 is a frontal cross-section through the trocar sleeve according to FIG. 12 along the line XIII-XIII in FIG. 12;

DETAILED DESCRIPTION OF EXEMPLARY EMBODIMENTS

Figure 1:
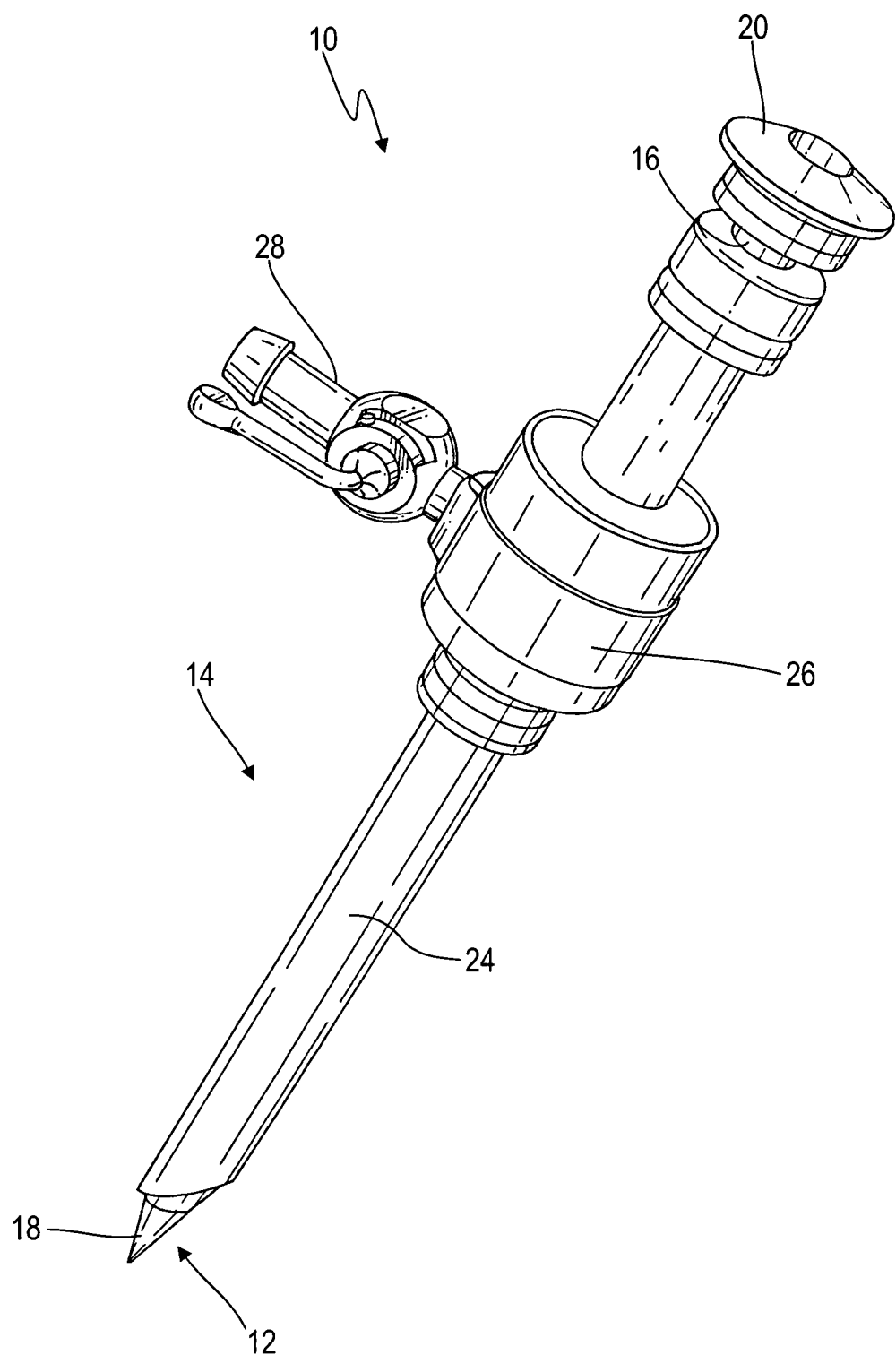
FIG. 1 is a perspective view of a trocar system.

With reference to FIG. 1, a conventional arrangement of a trocar system 10 will be elucidated. The trocar system 10 is generally referred to as trocar. The trocar system 10 comprises a trocar mandrel 12 and a trocar sleeve 14 that is insertable in the trocar mandrel 12 to introduce the trocar system 10 in a body opening, for instance in the abdominal region. The trocar system 10 comprises an elongated shape wherein the trocar mandrel 12 and the trocar sleeve 14 comprise a common longitudinal axis.

The trocar mandrel 12 comprises a shaft 16 at the distal end thereof a tip 18 is formed. At the proximal end of the shaft 16 of the trocar mandrel 12, a handling section 20 is formed.

The trocar sleeve 14 comprises a hollow shaft 24 that may also be referred to as tube. The trocar sleeve 14 further comprises a handling head 26 that is arranged at a proximal end of the trocar sleeve 14 or at least adjacent thereto. By way of example, the handling head 26 comprises a port 28 that is provided with a valve through which irrigation fluids, gases and such like may be supplied and led away.

The trocar system 10 elucidated in FIG. 1 comprises a rigid trocar sleeve 14, for instance a trocar sleeve 14 having a rigid hollow shaft 24. Further, trocar systems are known that comprise trocar sleeves that are, at least sectionally, arranged to be flexible and bendable. This may be helpful for feeding through bent instruments.

With reference to FIGS. 2 to 13 several exemplary embodiments of trocar systems and respective of trocar sleeves will be elucidated the hollow shafts of which are arranged to be flexible and deflectable. In exemplary embodiments, the trocar sleeves described hereinafter are manufactured from an elastomer material having a defined maximum Shore hardness value. Further, the trocar sleeves are integrally manufactured and integrate several components without the need of a multi-part structure.

The exemplary embodiments elucidated hereinafter relate to several aspects of the design and manufacture of trocar systems. It goes without saying that single features which are provided at one of the embodiments may also be transferred to other embodiments, and in fact isolated from other features of the respective exemplary embodiments.

With reference to FIGS. 2 and 3 a first embodiment of a trocar sleeve that is in its entirety designated by 40 will be elucidated in more detail. Similarly to what is shown in FIG. 1, the trocar sleeve 40 may be combined with a trocar mandrel to form a trocar system.

The trocar sleeve 40 comprises a hollow shaft 42 and a handling head 44. The hollow shaft 42 and the handling head 44 are integrally shaped and manufactured in one piece. The handling head 44 and the hollow shaft 42 together define a longitudinal extension of the trocar sleeve 40, refer also to a longitudinal axis that is designated in FIG. 3 by 68. The hollow shaft 42 defines a passage 46 extending in the longitudinal direction that is intended to accommodate a trocar mandrel or an instrument.

The hollow shaft 42 further comprises a distal end 48 and a proximal end 50. The distal end 48 is the end that is facing the interior of the patient when the trocar sleeve 40 is placed at a tissue section, for instance at an abdominal wall of the patient. The proximal end 50 is in this state facing the user or operating surgeon and accordingly facing away from the interior of the patient. At the proximal end 50 of the hollow shaft 42, the handling head 44 is formed.

In exemplary embodiments, the hollow shaft 42 comprises, at least sectionally, a smooth surface 52 that is not arranged as a corrugated surface and/or a curly surface. Nevertheless, at least in accordance with some embodiments, at the hollow shaft 42 a thread section 54 is formed that comprises, for instance, at least one thread turn 56 which may also be referred to as helix. Preferably, also the thread section 54 is shaped as an integral component of the trocar sleeve 40. In this connection, reference is made to the broken cross-sectional view according to FIG. 3. It is apparent that the hollow shaft 42, the handling head 44 and, is present, the thread section 54 are formed in one piece.

The pitch and the height of the turn of the thread 56 may be variable and may consider specific operating conditions. This may involve a huge pitch at a distal run-out of the turn of the thread 56. At a proximal run-out of the turn of the thread 56, however, a significantly reduced pitch may be provided. Similarly, the thread turn 56 may comprise, at its distal end, a very small height gradually developing to a maximum height, wherein a greater reduction of the height (per circumferential section) is present towards the proximal end of the thread turn 56. This arrangement may have the effect that the trocar sleeve 40, on the one hand, may be easily inserted in tissue as the distal end of the thread turn 56 is, so to say, shaped as an insertion aid. The pitch of the thread turn 56 is reduced towards the proximal end of the thread turn 56, and, further, a considerable height is still present. In this way, the hollow shaft 42 that is provided with the thread section 54 is well secured against a displacement towards the proximal end. It goes without saying that the arrangement of the thread section 54 elucidated herein is merely exemplary.

In some embodiments, it is conceivable to manufacture the trocar sleeve 40 integrally and by casting from a flexible material, such as an elastomer material, for instance. This enables a great freedom of design and, in some embodiments, the formation of additional components. In some embodiments, with the selected materials, there is no great likelihood of a formation of cavities/shrinking and such like. Hence, not in each case great care has to be applied to provide a more or less constant wall thickness. This applies in particular also to the thread section 54. Accordingly, both the surface at the outer side of the hollow shaft 42 and an inner contour 72 (refer to FIG. 3) at an inner side of the hollow shaft 52 may be smoothly shaped.

Taken in combination, it can be seen from FIGS. 2 and 3 that the handling head 44 nevertheless may comprise a rib structure to provide, on the one hand, a great stability, and to avoid, on the other hand, material accumulations.

The handling head 44 is radially enlarged with respect to the hollow shaft 42 and also provides an increased receiving opening. Further, the handling head 44 is provided with basically axially extending ribs 58 and with basically circumferentially extending ribs 60. The axial ribs 58 and the circumferential ribs 60 form a cross structure. The ribs 58, 60 define and/or surround recesses or depressions 62 that contribute to the prevention of material accumulations and/or to weight reduction, and to the optimization of the weight distribution. The hollow shaft 42 comprises a cylindrical wall 70 that surrounds the longitudinal axis 68. At the inner side of the wall 70, the inner contour 72 is formed.

The embodiment of the trocar sleeve 40 elucidated with reference to FIG. 3 further comprises, at the handling head 44, a groove-shaped mount 74, that may for instance serve for receiving a seal. The handling head 44 leads to a proximal termination surface 66 upstream of which, however, the mount 74 may be provided.

With reference to the longitudinal cross-section shown in FIG. 3, characteristic dimensions of the trocar sleeve 40 will be elucidated. A distal inner diameter of the hollow shaft 42 is denoted by $D_{di}$. A proximal inner diameter of the hollow shaft 42 is denoted by $D_{pi}$. A thickness of the wall 70 at the distal end 48 is denoted by $t_d$. A thickness of the wall 70 at the proximal end of the hollow shaft 42 is denoted by $t_p$.

Embodiments may be envisaged wherein the inner contour 72 of the hollow shaft 42 comprises along its longitudinal extension a basically constant cross-section ($D_{di}=D_{pi}$). However, also embodiments may be envisaged, wherein $D_{di}<D_{pi}$ applies. In accordance with this embodiment, the inner contour 72 is for instance conical or spherically shaped and provided with a tapering towards the distal end 48.

In accordance with alternative or additional arrangements, the thickness of the wall 70 along the longitudinal extension of the hollow shaft 72 is basically constant ($t_d=t_p$). However, there are also arrangements conceivable, refer for instance to the embodiment shown in FIG. 3, wherein the wall thickness of the wall 70 is increased from the distal end 48 towards the proximal end 50 ($t_d<t_p$). Any of the afore-mentioned embodiments may be combined with one another.

It is essential that the inner contour 72 is adapted to the outer contour of a trocar mandrel such that a widening of the hollow shaft 72 is generated in the desired manner when the trocar mandrel is inserted in the trocar sleeve 40. Therefore, in some embodiments, at least one of the hollow shaft 42 and the trocar mandrel is at least sectionally tapered, conically or spherically shaped.

In this connection, additional reference is made to the FIGS. 4, 5 and 6 which elucidate a trocar system 76 that comprises a trocar sleeve 40, for instance in accordance with the FIGS. 2 and 3, and a trocar mandrel denoted by 80.

As already elucidated in connection with FIG. 1, the trocar mandrel 80 comprises at its distal end a tip 82 and at its proximal end that is facing away from the distal end, a handling section 84. A shaft 86 extends between the tip 82 and the handling section 84. At the shaft 86, a circumferential contour or outer contour 88 is formed that comes into contact with the inner contour 72 of the hollow shaft 42 of the trocar sleeve 40.

In FIG. 4, proximal dimension and/or a proximal diameter of the outer contour 88 is indicated by $D_{pe}$. In FIG. 5, a distal dimension and/or a distal diameter of the outer contour 88 is indicated by $D_{de}$. In accordance with at least some embodiments, $D_{pe}=D_{de}$ applies to the trocar mandrel 80. Accordingly, the shaft 86 of the trocar mandrel 80 is, at least along substantial sections of its longitudinal extension, cylindrically shaped and hence comprises a constant cross-section. However, there are also arrangements conceivable wherein $D_{de}<D_{pe}$ applies. Accordingly, also the shaft 86 of the trocar mandrel 80 may be at least sectionally tapered in a conical or spherical manner towards its distal end. It goes without saying that in addition the tip 82 is provided. Accordingly, it is conceivable that at least the inner contour 72 or the outer contour 88 are tapered towards the distal end. It is however also conceivable to form both the inner contour 72 and the outer contour 88 cylindrically with constant cross-sections. Further, it is to be noted that the cross-sections of the inner contour 72 and/or the outer contour 88 do not necessarily have to be circularly shaped. Also cross-sections that are oval or that deviate in another fashion from a pure circular shape are also conceivable. Insofar, the indications $D_{di}$, $D_{pi}$, $D_{de}$ and $D_{pe}$ do not necessarily have to be interpreted as diameter indications.

FIG. 4 shows a state of the trocar system 76 wherein the trocar mandrel 80 is inserted in the trocar sleeve 40 but not yet entirely led through the sleeve 40, refer an offset dimension $O_1$ in FIG. 4 between the distal end 48 of the trocar sleeve 40 and the tip 82 of the trocar mandrel 80. Further, an insertion direction is to be noted in FIG. 4 by 92.

In FIG. 5, the trocar mandrel 80 is entirely inserted in the trocar sleeve 40 so that the tip 82 extends beyond the distal end 48 of the hollow shaft 42, refer to an offset dimension denoted by $O_2$ in FIG. 5. Further, the handling section 84 of the trocar mandrel 80 abuts the handling head 44 of the trocar sleeve 40 in FIG. 5. The handling section 84 contacts the proximal termination surface 66 of the handling head 44.

In accordance with substantial aspects of the present disclosure, the trocar mandrel 80 widens the hollow shaft 42 of the trocar sleeve 40 while the trocar mandrel 80 is inserted in the trocar sleeve 40 and/or when the trocar mandrel 80 is entirely inserted therein. Radial expansion of the hollow shaft 42 is elucidated in FIG. 5 by arrows denoted by 94. In other words, the outer contour 88 of the trocar mandrel 80 is having a certain "excess" size, compared to the inner contour 72 of the hollow shaft 42 so that the "soft" hollow shaft 42 is widened. In this way, at the hollow shaft 42, particularly in the region of the inner contour 72 that is in direct contact with the outer contour 88, tensions are generated. Tensions of this kind effect a stabilization of the as such soft, elastic trocar sleeve 40. The hollow shaft 42 is mounted at the trocar mandrel 80 in a preloaded manner. In this way, when placing the trocar, for instance a compression or an expansion of the hollow shaft 42 in the direction of its longitudinal extension is efficiently reduced and/or nearly prevented. The same implies to a twisting (torsion) of the hollow shaft 42 about its longitudinal axis.

In FIG. 6, the "excess size" of the trocar mandrel 80 with respect to the inner contour 72 of the hollow shaft 42 in an intersection region is indicated, refer to the outer dimension (outer diameter $D_e$) of the trocar mandrel 80 and the inner dimension (inner diameter $T_i$) of the hollow shaft 42. A desired excess size may be defined by an appropriate design of the inner contour 72 and the outer contour 88 which results in a defined preloading at the hollow shaft 42. As already indicated herein before, several arrangements are conceivable, involving cylindrical, conical and/or spherical shapes, to cause the desired tension characteristic. This may relate to a ratio between the achieved preloading at the hollow shaft 72 and the present axial position of the trocar mandrel 80 with respect to the trocar sleeve 40.

FIG. 7 elucidates a modified embodiment of a trocar sleeve that is denoted by 140. The trocar sleeve 140 is basically arranged in a fashion similar to the trocar sleeve 40 elucidated with reference to FIGS. 2 to 6. The trocar sleeve 140 is provided with a hollow shaft 42 and a handling head 44, as already described herein before. At a proximal end of the handling head 44, a seal 100 is formed, that comprises a circumferential sealing contour 102 and/or sealing lip. It can be seen from the hatching of the longitudinal cross-section through the trocar sleeve 140 according to FIG. 7 that the seal 100 is formed as an integral component of the trocar sleeve 140. As the trocar sleeve 140 is integrally manufactured from an elastomer material, also sealing arrangements may be integrated and formed in one piece with the hollow shaft 42 and the handling head 44.

With reference to FIGS. 8 and 9, a further embodiment of a trocar sleeve is elucidated which is denoted by 240. Also the trocar sleeve 240 is arranged basically similar to the trocar sleeve 40 and provided with a hollow shaft 42 and a handling head 44. Further, by way of example, a thread section 54 is formed.

It can be seen from the cross-sectional view in FIG. 9 that a thickness of the wall 70 of the hollow shaft 42 from the distal end 48 towards the proximal end 50 significantly increases, refer the dimensions $t_d$ and $t_p$. Hence, a desired strength behavior and/or preloading behavior along the longitudinal axis of the hollow shaft 42 may be achieved, when a trocar mandrel is inserted in the trocar sleeve 240.

As a modification with respect to the exemplary embodiments elucidated herein before, the handling head 44 in FIG. 8 and FIG. 9 is compact shaped and not provided with stiffeners. Also such a design is conceivable. At the handling head 44, a sealing receiving contour 74 and/or mount for a seal is formed, refer to FIG. 9. Starting at the hollow shaft 42, the handling head 44 comprises a concave transition 106. Further, rib-shaped elevations 108 are formed; refer in this context also to FIG. 10 which will be described in more detail further below. The exemplary embodiment shown in FIGS. 8 and 9 comprises two rib-shaped elevations 108 that are offset from one another by 180°, and that are elevated with respect to the concave transition 106. The handling head 44 terminates in a proximal termination surface 110 upstream of which, however, the mount may be provided.

Figure 10:
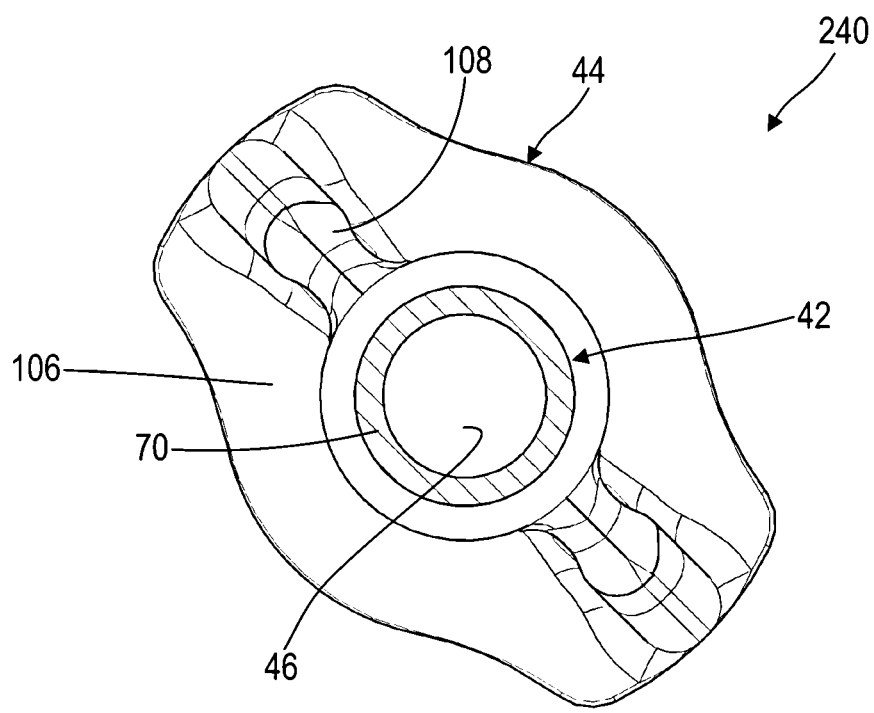
FIG. 10 is a frontal cross-section through the trocar sleeve according to FIG. 9, wherein the view orientation is indicated in FIG. 9 by a line X-X.

FIG. 10 elucidates an axial cross-section through the trocar sleeve 240 elucidated with reference to FIGS. 8 and 9. In FIG. 9, a line X-X indicates the curve of the cross-section. By the insertion of the trocar mandrel, the wall 70 of the hollow shaft 42 may be widened. In FIG. 10, the wall 70 surrounds a circular passage 46. It goes without saying that also other profiles are conceivable.

Figure 11:
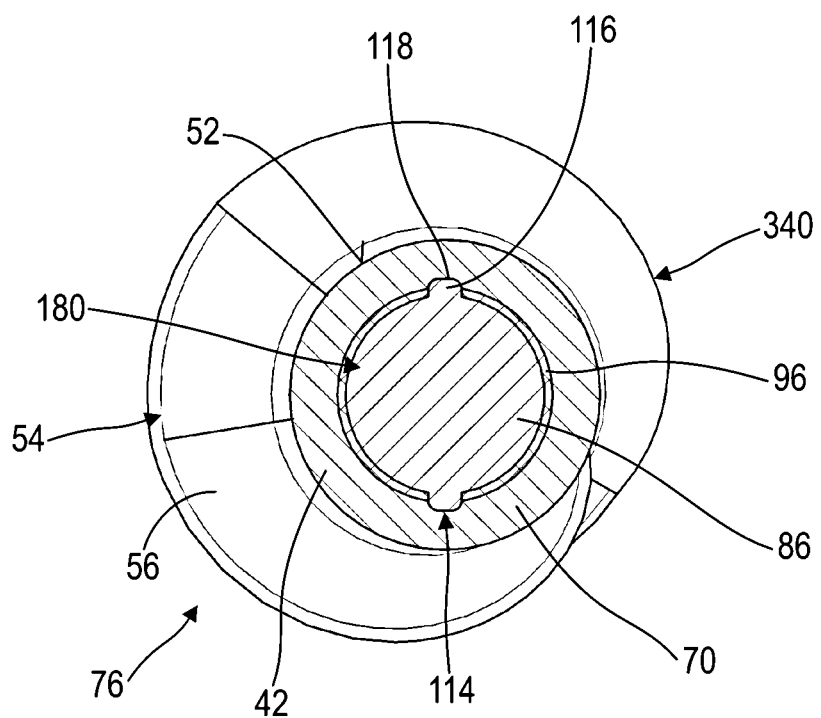
FIG. 11 is a frontal cross-section through a trocar system, comprising a trocar sleeve and a trocar mandrel, wherein the view orientation is elucidated in FIG. 9 by a line designated by XI-XI.

In this connection, additional reference is made to FIG. 11 that elucidates a further axial cross-section through a trocar sleeve that is denoted by 340. In the trocar sleeve 340, a trocar mandrel 180 is accommodated. The embodiment of the trocar sleeve 340 elucidated with reference to FIG. 11 does not entirely correspond to the arrangement of the trocar sleeve 240 according to FIG. 9. Nevertheless, primarily for illustrative purposes, in FIG. 9 a curve of the cross-section is indicated by a line denoted by XI-XI.

FIG. 11 shows a view from the proximal end at the thread turn 56 of the thread section 54. As already elucidated herein before, a height of the thread turn 56 with respect to a surface 52 of the hollow shaft 42 is variable.

The trocar sleeve 340 and the trocar mandrel 180 in accordance with the arrangement of FIG. 11 differ from the embodiments described herein before by a rotation prevention feature 114. The rotation prevention feature 114 comprises at least one position securing element 116 at the trocar mandrel 180. At the trocar sleeve 340, the rotation prevention feature 114 comprises at least one position securing element 118. The position securing element 116 may be arranged as an elevation extending in the longitudinal direction. The position securing element 118 may be arranged as a depression extending in the longitudinal direction that is adapted to the elevation. In FIG. 11, the rotation prevention feature 114 comprises two respective pairs of position securing elements 116, 118 that are displaced by 180°.

When, for instance due to external forces, either the trocar sleeve 340 or the trocar mandrel 180 are respectively rotated with respect to the other component, in the region of the position securing elements 116, 118, for instance, an increase of the preloading at the hollow shaft 42 is caused when the position securing elements 116, 118 tend to disengage. This results in a considerable local widening and hence in a further increase of the inherent stability of the hollow shaft 42 of the trocar sleeve 340. In other words, the increase of the stability of the hollow shaft 42 is the greater the greater the as such deforming moment is.

It goes without saying that the rotation prevention feature 114 may involve also other embodiments of position securing elements 116, 118. For instance, profiles of the inner contour 72 and the outer contour 88 may be oval shaped or in another way shaped non-circular.

With additional reference to FIGS. 12 and 13, a further embodiment of a trocar sleeve will be elucidated that is denoted by 440. The trocar sleeve 440 is basically formed in accordance with the arrangement of the trocar sleeve 40 elucidated with reference to FIGS. 2 to 6.

FIG. 13 elucidates an axial cross-section through the trocar sleeve 440 that is represented, for illustrative purposes, in the perspective view of FIG. 12 by a line XIII-XIII.

The trocar sleeve 440 primarily differs from the arrangements in accordance with FIGS. 2 to 6 by the shape of the handling head 44. The handling head 44 of the trocar sleeve 440 is compact shaped and not provided with ribs or depressions. Insofar, although the handling head 44 comprises material accumulations, this is, however, not necessarily detrimental with the selected materials and/or manufacturing processes. It can be seen from the frontal view of FIG. 13 that the handling head 44 comprises a thickening 122, wherein elevations 124 are provided that extend from the thickening 122 radially outwards. By way of example, two elevations 124 are provided that are displaced by 180°. The elevations 124 respectively comprise an entrainment flank 126 through which a force may be transmitted, for instance to rotate the trocar sleeve 440, refer to an arrow denoted by 128 in FIG. 12 that elucidates the rotation direction. In this way, the trocar sleeve 440, or a trocar system comprising the trocar sleeve 440 and a trocar mandrel accommodated therein, may be operated, for instance to screw in the thread section 54. In this way, the insertion of the trocar system is facilitated.

In regard of the elevations 124 that are provided with respective entrainment flanks 126, it is to be noted that also the trocar sleeve 40 in FIG. 2 comprises at least a similar design, wherein the thickening (122 in FIG. 12) is simply replaced by ribs 58 and recesses 62 there.

Figure 14:
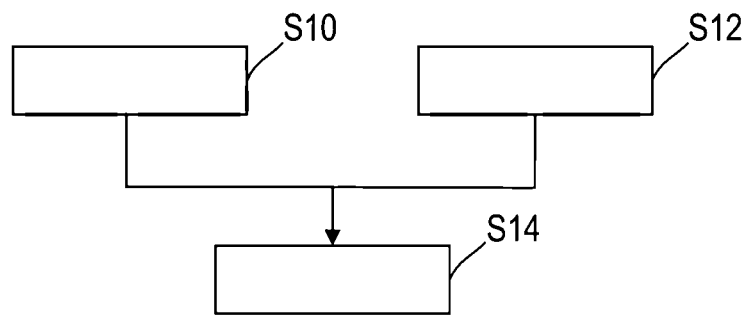
FIG. 14 is a schematic block diagram elucidating a method of manufacturing a trocar sleeve.

With reference to FIG. 14, an exemplary embodiment of a method for manufacturing a trocar sleeve will be elucidated by means of a block diagram. The method involves a step S10 that comprises the provision of a mold that is arranged for forming a trocar sleeve including a flexible hollow shaft and a handling head. The mold generally comprises at least one cavity which, so to say, represents a negative of the desired trocar sleeve. In a further step S12, an elastomer material is provided. In some embodiments, a material is provided that comprises, in the processed/molded state, a certain defined Shore hardness. A sufficient flexibility is present in a material having a Shore hardness, determined in accordance with International Standard ISO 7619-1 (ISO 7619-1:2010), of no more than 90 Shore A. In certain embodiments, the Shore hardness is less than 70 Shore A. In certain embodiments, the Shore hardness is less than 50 Shore A. In an exemplary embodiment, the Shore hardness is 70 Shore A, or approximately 70 Shore A.

A further step S14 that relates to the manufacture of the trocar sleeve by casting or molding follows on the steps S10 and S12. The step S14 involves filling the mold with an appropriate starting material. The casting or molding further involves integrally forming the hollow shaft and the handling head. At the hollow shaft, an inner contour is selected that is adapted to an outer contour of a trocar mandrel in such a way that the trocar sleeve and the trocar mandrel are arranged to be coupled with one another while generating a defined preloading to guide the trocar sleeve in a defined manner.

Figure 15:
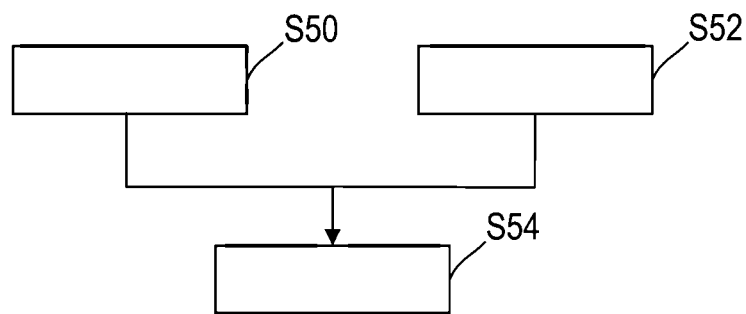
FIG. 15 is a schematic block diagram elucidating a method of providing a trocar system.

With reference to FIG. 15, a method of providing a trocar system is elucidated by means of a block diagram. The method involves a step S50 that involves manufacturing a trocar sleeve, for instance in accordance with manufacturing method elucidated with reference to FIG. 14. The method comprises a further step S52 that involves the provision of a trocar mandrel that is adapted to the trocar sleeve. In some embodiments, the trocar mandrel comprises an outer contour that is adapted to an inner contour of the hollow shaft of the trocar sleeve. This may involve arrangements wherein the outer contour of the trocar mandrel is deliberately selected to be somewhat larger than the inner contour of the hollow shaft.

Eventually a step S54 follows that relates to an insertion of the trocar mandrel in the trocar sleeve, wherein the trocar sleeve is at least sectionally widened. This involves the generation of a defined preloading in the hollow shaft of the trocar sleeve. This may be used for mechanically stabilizing the trocar sleeve in combination with the trocar mandrel.

What is claimed is:

1. A trocar system comprising:
   a trocar sleeve having a hollow shaft and a handling head, the hollow shaft comprises a distal end and a proximal end and is flexible from the distal end to the proximal end, the handling head is disposed at the proximal end of the hollow shaft, the trocar sleeve is manufactured from an elastomer material, and
   a trocar mandrel that is insertable into the trocar sleeve,
   wherein the trocar system has an unloaded state where the trocar mandrel is separated from the hollow shaft and a mounted state where the trocar mandrel is inserted in the hollow shaft,
   wherein in the unloaded state, an inner contour of the hollow shaft is smaller than an outer contour of the trocar mandrel,
   wherein in the mounted state, the inner contour of the hollow shaft is at least sectionally expanded by the outer contour of the trocar mandrel such that an interaction between the trocar sleeve and the trocar mandrel generates a defined preloading in a longitudinal direction of the hollow shaft, thereby stabilizing and stiffening the trocar sleeve in the longitudinal direction.

2. The trocar system as claimed in claim 1, wherein in the mounted state, the hollow shaft is, in a defined axial relative position between the trocar sleeve and the trocar mandrel, at least sectionally widened by the trocar mandrel.

3. The trocar system as claimed in claim 1, wherein the elastomer material of the trocar sleeve has a Shore hardness, determined in accordance with ISO 7619-1, of no more than 90 Shore A.

4. The trocar system as claimed in claim 3, wherein the Shore hardness is about 70 Shore A.

5. The trocar system as claimed in claim 1, wherein the hollow shaft and the handling head are formed in one piece.

6. The trocar system as claimed in claim 1, wherein the trocar sleeve is integrally shaped and manufactured by molding.

7. The trocar system as claimed in claim 1, wherein the elastomer material is selected from the group consisting of: silicone, silicone rubber, thermoplastic elastomers, rubber, and compounds containing the same.

8. The trocar system as claimed in claim 1, wherein the hollow shaft is, at least sectionally, tubular or cylindrically shaped.

9. The trocar system as claimed in claim 1, wherein the hollow shaft comprises, at least sectionally, a smooth, elevation-free outer surface.

10. The trocar system as claimed in claim 1, wherein the hollow shaft is, at least partially, provided with a friction-reducing coating.

11. The trocar system as claimed in claim 1, wherein the hollow shaft comprises, at least sectionally, a wall thickness increasing from the distal end to the proximal end.

12. The trocar system as claimed in claim 1, wherein the inner contour of the hollow shaft is, at least sectionally, tapered or spherically shaped, and wherein the inner contour has an inner diameter that is increasing from the distal end to the proximal end.

13. The trocar system as claimed in claim 12, wherein the inner contour of the hollow shaft is adapted to an at least sectionally tapered or spherical shape of the outer contour of the trocar mandrel to prestress the trocar sleeve when the trocar mandrel is advanced in the hollow shaft towards the distal end.

14. The trocar system as claimed in claim 1, wherein the trocar sleeve further comprises a thread section that is formed at the hollow shaft, wherein the hollow shaft, the thread section and the handling head are formed in one piece.

15. The trocar system as claimed in claim 1, wherein the inner contour of the hollow shaft is, at least sectionally, non-rotationally symmetric, and provided with a non-circular cross-section.

16. The trocar system as claimed in claim 1, wherein one of a sealing contour and a sealing receiving contour is formed at the proximal end of the hollow shaft ink in a vicinity of the handling head.

17. The trocar system as claimed in claim 1, wherein, from the unloaded state, a defined interference between the inner contour of the hollow shaft and the outer contour of the trocar mandrel is present upon insertion of the trocar mandrel into the trocar sleeve.

18. The trocar system as claimed in claim 1, wherein in the mounted state, the inner contour of the hollow shaft is in contact with the outer contour of the trocar mandrel for stabilizing and stiffening the trocar sleeve.

* * * * *

UNITED STATES PATENT AND TRADEMARK OFFICE
CERTIFICATE OF CORRECTION

PATENT NO. : 10,856,860 B2  
APPLICATION NO. : 15/416257  
DATED : December 8, 2020  
INVENTOR(S) : Sebastian Wagner, Michael Sauer and Alexander Fuchs Page 1 of 1

It is certified that error appears in the above-identified patent and that said Letters Patent is hereby corrected as shown below:

On the Title Page

Column 1, (71) Applicant:  
"Karl Storz GmbH & Co. KG, Tuttlingen (DE)"

Should read:  
--Karl Storz SE & Co. KG, Tuttlingen (DE)--

Column 1, (73) Assignee:  
"Karl Storz GmbH & Co. KG, Tuttlingen (DE)"

Should read:  
--Karl Storz SE & Co. KG, Tuttlingen (DE)--

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*